(12) United States Patent
Jacofsky et al.

(10) Patent No.: US 9,744,372 B2
(45) Date of Patent: Aug. 29, 2017

(54) THERAPEUTIC APPLICATIONS OF COLD PLASMA

(71) Applicant: Plasmology4, Inc., Scottsdale, AZ (US)

(72) Inventors: Marc C. Jacofsky, Phoenix, AZ (US);
David J. Jacofsky, Peoria, AZ (US);
Robert M. Hummel, Cave Creek, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 0 days.

(21) Appl. No.: 15/257,298

(22) Filed: Sep. 6, 2016

(65) Prior Publication Data

US 2016/0375263 A1    Dec. 29, 2016

Related U.S. Application Data

(62) Division of application No. 14/026,679, filed on Sep. 13, 2013, now Pat. No. 9,440,057.

(60) Provisional application No. 61/701,095, filed on Sep. 14, 2012, provisional application No. 61/787,417, filed on Mar. 15, 2013.

(51) Int. Cl.
*A61N 1/44* (2006.01)
*A61B 18/04* (2006.01)
*A61M 37/00* (2006.01)

(52) U.S. Cl.
CPC .............. *A61N 1/44* (2013.01); *A61B 18/042* (2013.01); *A61M 37/00* (2013.01)

(58) Field of Classification Search
USPC .............................................. 607/3; 604/290
See application file for complete search history.

(56) References Cited

U.S. PATENT DOCUMENTS

| | | |
|---|---|---|
| 2,927,322 A | 3/1960 | Simon et al. |
| 3,432,722 A | 3/1969 | Naydan et al. |
| 3,487,414 A | 12/1969 | Booker |
| 3,735,591 A | 5/1973 | Burkhart |
| 4,088,926 A | 5/1978 | Fletcher et al. |
| 4,365,622 A | 12/1982 | Harrison |
| 4,380,320 A | 4/1983 | Hollstein et al. |
| 4,422,013 A | 12/1983 | Turchi et al. |
| 5,079,482 A | 1/1992 | Villecco et al. |

(Continued)

FOREIGN PATENT DOCUMENTS

| | | |
|---|---|---|
| WO | WO 2005/084569 A1 | 9/2005 |
| WO | WO 2006/116252 A2 | 11/2006 |

(Continued)

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

(Continued)

*Primary Examiner* — Nicole F Johnson
(74) *Attorney, Agent, or Firm* — Sterne, Kessler, Goldstein & Fox P.L.L.C.

(57) ABSTRACT

The present disclosure relates to methods of treating diseases and disorders comprising applying a therapeutically effective dose of cold plasma. In particular examples, the diseases and disorders include, but are not limited to, diseases and disorders of the skin, musculoskeletal, and immune systems.

12 Claims, 8 Drawing Sheets

(56) References Cited

U.S. PATENT DOCUMENTS

Figure 1:
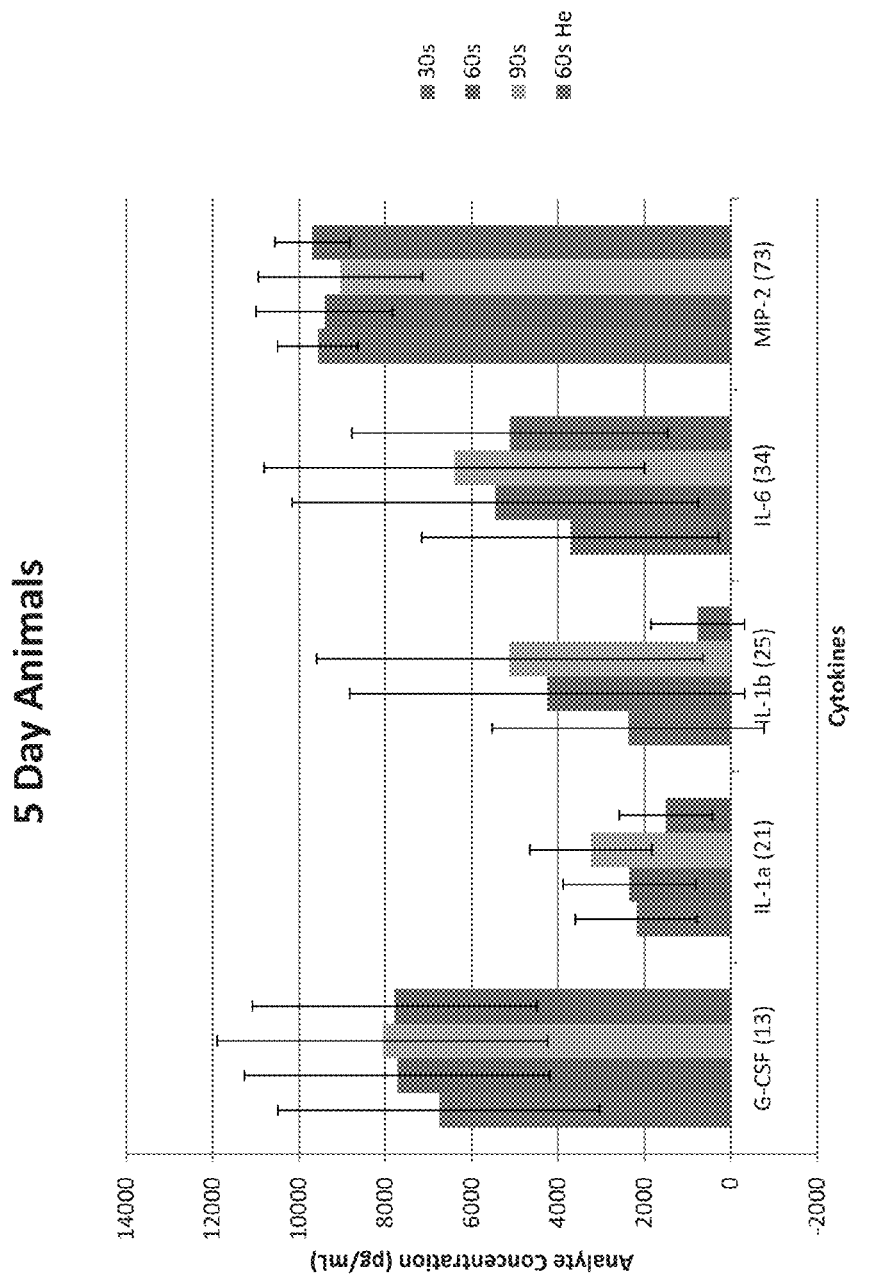

| | | |
|---|---|---|
| 5,216,330 A | 6/1993 | Ahonen |
| 5,225,740 A | 7/1993 | Ohkawa |
| 5,304,888 A | 4/1994 | Gesley et al. |
| 5,698,164 A | 12/1997 | Kishioka et al. |
| 5,876,663 A | 3/1999 | Laroussi |
| 5,883,470 A | 3/1999 | Hatakeyama et al. |
| 5,909,086 A | 6/1999 | Kim et al. |
| 5,961,772 A | 10/1999 | Selwyn |
| 5,977,715 A | 11/1999 | Li et al. |
| 6,096,564 A | 8/2000 | Denes et al. |
| 6,113,851 A | 9/2000 | Soloshenko et al. |
| 6,204,605 B1 | 3/2001 | Laroussi et al. |
| 6,225,593 B1 | 5/2001 | Howieson et al. |
| 6,228,330 B1 | 5/2001 | Herrmann et al. |
| 6,262,523 B1 | 7/2001 | Selwyn et al. |
| 6,441,554 B1 | 8/2002 | Nam et al. |
| 6,474,060 B2 | 11/2002 | Khair |
| 6,611,106 B2 | 8/2003 | Monkhorst et al. |
| 6,667,007 B1 | 12/2003 | Schmidt |
| 6,956,329 B2 | 10/2005 | Brooks et al. |
| 6,958,063 B1 | 10/2005 | Soll et al. |
| 7,006,874 B2 | 2/2006 | Knowlton et al. |
| 7,017,790 B1 | 3/2006 | Ruan et al. |
| 7,081,711 B2 | 7/2006 | Glidden et al. |
| 7,094,314 B2 | 8/2006 | Kurunczi |
| 7,192,553 B2 | 3/2007 | Crowe et al. |
| 7,215,697 B2 | 5/2007 | Hill |
| 7,271,363 B2 | 9/2007 | Lee et al. |
| 7,300,436 B2 | 11/2007 | Penny et al. |
| 7,608,839 B2 | 10/2009 | Coulombe et al. |
| 7,633,231 B2 | 12/2009 | Watson |
| 7,683,342 B2 | 3/2010 | Morfill et al. |
| 7,691,101 B2 | 4/2010 | Davison et al. |
| 7,719,200 B2 | 5/2010 | Laroussi |
| 7,777,151 B2 | 8/2010 | Kuo |
| 7,785,322 B2 | 8/2010 | Penny et al. |
| 8,005,548 B2 | 8/2011 | Watson |
| 8,267,884 B1 | 9/2012 | Hicks |
| 8,294,369 B1 | 10/2012 | Laroussi |
| 8,460,283 B1 | 6/2013 | Laroussi et al. |
| 2002/0129902 A1 | 9/2002 | Babayan et al. |
| 2003/0222586 A1 | 12/2003 | Brooks et al. |
| 2005/0088101 A1 | 4/2005 | Glidden et al. |
| 2005/0179395 A1 | 8/2005 | Pai |
| 2006/0189976 A1 | 8/2006 | Karni et al. |
| 2008/0159925 A1 | 7/2008 | Shimizu et al. |
| 2009/0188626 A1 | 7/2009 | Lu et al. |
| 2009/0209958 A1* | 8/2009 | Davison ............ A61B 18/1402 606/41 |
| 2010/0087812 A1 | 4/2010 | Davison et al. |
| 2010/0133979 A1 | 6/2010 | Lu |
| 2010/0145253 A1 | 6/2010 | Gutsol et al. |
| 2011/0022043 A1 | 1/2011 | Wandke et al. |
| 2011/0230819 A1 | 9/2011 | Watson |
| 2012/0089103 A1* | 4/2012 | Tel-Ari ................ A61M 35/00 604/290 |
| 2012/0100524 A1 | 4/2012 | Fridman et al. |
| 2012/0135390 A1 | 5/2012 | Clyne et al. |
| 2012/0187841 A1 | 7/2012 | Kindel et al. |
| 2012/0259270 A1 | 10/2012 | Wandke et al. |
| 2013/0022514 A1 | 1/2013 | Morfill et al. |
| 2013/0053762 A1 | 2/2013 | Rontal et al. |
| 2013/0068226 A1 | 3/2013 | Watson et al. |
| 2013/0068732 A1 | 3/2013 | Watson et al. |
| 2013/0069530 A1 | 3/2013 | Watson et al. |
| 2013/0071286 A1 | 3/2013 | Watson et al. |
| 2013/0072152 A1 | 3/2013 | Ota |
| 2013/0072858 A1 | 3/2013 | Watson et al. |
| 2013/0072859 A1 | 3/2013 | Watson et al. |
| 2013/0072860 A1 | 3/2013 | Watson et al. |
| 2013/0072861 A1 | 3/2013 | Watson et al. |
| 2013/0134878 A1 | 5/2013 | Selwyn |
| 2013/0199540 A1 | 8/2013 | Buske |
| 2014/0171854 A1 | 6/2014 | Jacofsky et al. |

FOREIGN PATENT DOCUMENTS

| | | |
|---|---|---|
| WO | WO 2010/107744 A1 | 9/2010 |
| WO | WO 2010/107745 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |

OTHER PUBLICATIONS

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http//www.physorg.com/printnews.php?newsid=6688>.

Book of Abstracts 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, Wiley-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

International Search Report mailed Nov. 27, 2012 for Appl. No. PCT/US2012/055607, 3 pages.

Written Opinion of International Searching Authority mailed Nov. 27, 2012 for Appl. No. PCT/US2012/055607, 6 pages.

Fridman et al., "Comparison of Direct and indirect Effects of Non-Thermal Atmospheric-Pressure Plasma on Bacteria," *Plasma Process Polym.*, 4, 370-375. 6 pages, Wiley-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci el al., "The effect of stochastic electrical noise on hard-to-heal wounds," *Journal of Wound Care*, 8 pages, 19:3 Mark Allen Publishing Ltd (Mar. 2010).

U.S. Appl. No. 61/485,747, filed May 13, 2011, inventor Thomas J. Sheperak, 14 pages.

(56) References Cited

OTHER PUBLICATIONS

Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11. 2011).

Pei et al., "Inactivation of a 25.5 μm *Enterococcus faecalis* biofilm by a roomtemperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

Fridman et al., "Use of non-thermal atmospheric pressure plasma discharge for coagulation and sterilization of surface wounds," *IEEE International Conference on Plasma Science*, p. 257, 1 page (Jun. 2005) (Abstract only).

Fridman et al., "Blood coagulation and living tissue sterilization by floating-electrode dielectric barrier discharge in air," *Plasma Chemistry and Plasma Processing*, 26:425-442, 18 pages, Springer (Aug. 2006).

Leduc et al., "Cell permeabilization using a non-thermal plasma," *New Journal of Physics*, 11 115021, 12 pages, IOP Publishing Ltd (Nov. 26, 2009).

Dinarello, C.A., "Proinflammatory Cytokines*," *Chest* 118(2):503-508, American College of Chest Physicians, United States (2000).

Fridman, G., et al., "Applied Plasma Medicine," *Plasma Process Polym.* 5:503-533, Wiley-VCH Verlag GmbH & Co., Germany (2008).

Kohn, et al., "Is Type 2 Diabetes an Autoimmune-Inflammatory Disorder of the Innate Immune System?," *Endocrinology* 146(10):4189-4191, The Endocrine Society, United States (2005).

Nair, A., "Prolotherapy for tissue repair" *Translational Research* 158(3): 129-131, Elsevier, United States (2011).

Su, D-L., et al., "Roles of Pro-and Anti-Inflammatory Cytokines in the Pathogenesis of SLE," *Journal of Biomedicine and Biotechnology* 2012: article ID 347141 pp. 1-15, Hindawi Publishing Corporation, United States (2012).

Opal, S.M., and Depalo, V.A., "Anti-Inflammatory Cytokines*," *Chest* 117(4):1162-1172, The American College of Chest Physicians, United States (2000).

International Search Report and Written Opinion mailed Feb. 14, 2014 for Appl. No. PCT/US2013/059725, 7 pages.

Co-Pending Applications, U.S. Appl. No. 14/142,333 inventors Jacofsky, M.C. et al., filed Dec. 27, 2013.

Co-Pending Applications, U.S. Appl. No. 14/145,320 inventors Jacofsky, M.C. et al., filed Dec. 31, 2013.

Co-Pending Applications, U.S. Appl. No. 14/145,312 inventors Jacofsky, M.C. et al., filed Dec. 31, 2013.

Co-Pending Applications, U.S. Appl. No. 14/145,297 inventors Jacofsky, M.C. et al., filed Dec. 31, 2013.

Co-Pending Applications, U.S. Appl. No. 14/145,898 inventors Watson, G.A. et al., filed Dec. 31, 2013.

Co-Pending Applications, U.S. Appl. No. 14/103,540 inventors Jacofsky, M.C. et al., filed Dec. 11, 2013.

\* cited by examiner

THERAPEUTIC APPLICATIONS OF COLD PLASMA

CROSS-REFERENCE TO RELATED APPLICATIONS

This application is a divisional of U.S. application Ser. No. 14/026,679, filed Sep. 13, 2013, which issued as U.S. Pat. No. 9,440,057 on Sep. 13, 2016, which claims the benefit of now-expired U.S. Provisional Application No. 61/701,095, filed Sep. 14, 2012, and now-expired U.S. Provisional Application No. 61/787,417, filed Mar. 15, 2013, each of which is incorporated by reference herein in its entirety.

BACKGROUND

Field of the Art

The present disclosure relates to methods of treating diseases and disorders comprising applying a therapeutically effective dose of cold plasma. In particular examples, the diseases and disorders include, but are not limited to, diseases and disorders of the skin, musculoskeletal, and immune systems.

Background Art

Plasma is a state of matter similar to gas in which a portion of the atoms or molecules are ionized. Atmospheric pressure hot plasmas are known to exist in nature. For example, lightning is an example of a dc arc (hot) plasma. Atmospheric pressure cold plasma processes are also known in the art. Generally, cold plasma contains high temperature electrons and ions and background gas that are close to room temperature. Most of the at or near atmospheric pressure cold plasma processes are known to utilize positive to negative electrodes in different configurations, which release free electrons in a noble gas medium.

Research into medical application of cold plasma has expanded with the development of new plasma sources. Contemplated medical applications include, for example, the use of cold plasma for the sterilization of surface wounds, enhancement of blood coagulation, promotion of wound healing, treatment of cancer, treatment of cavities, treatment of chronic foot and leg ulcers. See, e.g., PCT Pub. No WO 2010/107745, US 2012/0135390, 2010/0087812, and Fridman et al., *Plasma Process. Polym.* (2008) 5:503-533.

The present invention describes the surprising utilization of cold plasma for the treatment of diseases and disorders affecting subcutaneous tissues. Heretofore, cold plasma was used only for the treatment of surface wounds. That cold plasma can be used to treat subcutaneous tissues is a surprising and significant advancement to the technical field.

BRIEF SUMMARY OF THE INVENTION

In one aspect, the present invention pertains to methods of treating a skin disease or disorder in a subject in need thereof comprising applying a therapeutically effective dose of cold plasma, wherein the skin disease or disorder is associated with an autoimmune or inflammatory disease or disorder. In specific embodiments, the autoimmune or inflammatory disease or disorder is selected from the group consisting of systemic lupus erythematosus, cutaneous lupus erythematosus, scleroderma, psoriasis, dermatomyositis and dermatitis.

In another aspect, the present invention relates to methods of treating a musculoskeletal disease or disorder in a subject in need thereof comprising applying a therapeutically effective dose of cold plasma. In particular embodiments, the musculoskeletal disease or disorder is associated with an acute injury, chronic injury, chronic joint pain or an autoimmune or inflammatory disease or disorder.

In a further aspect, the present invention provides methods of suppressing subcutaneous inflammation in a subject in need thereof comprising applying a therapeutically effective dose of cold plasma.

In one embodiment, a method of treatment described herein comprises applying cold plasma locally to an affected area of the subject's body. In specific embodiments the affected area can be an affected skin area, joint, tendon, ligament or muscle. In another embodiment, a method of treatment described herein comprises applying cold plasma systemically to the subject's body.

BRIEF DESCRIPTIONS OF THE DRAWINGS

FIG. 1. Cytokines response present in tissue samples at 5 days.

Figure 2:
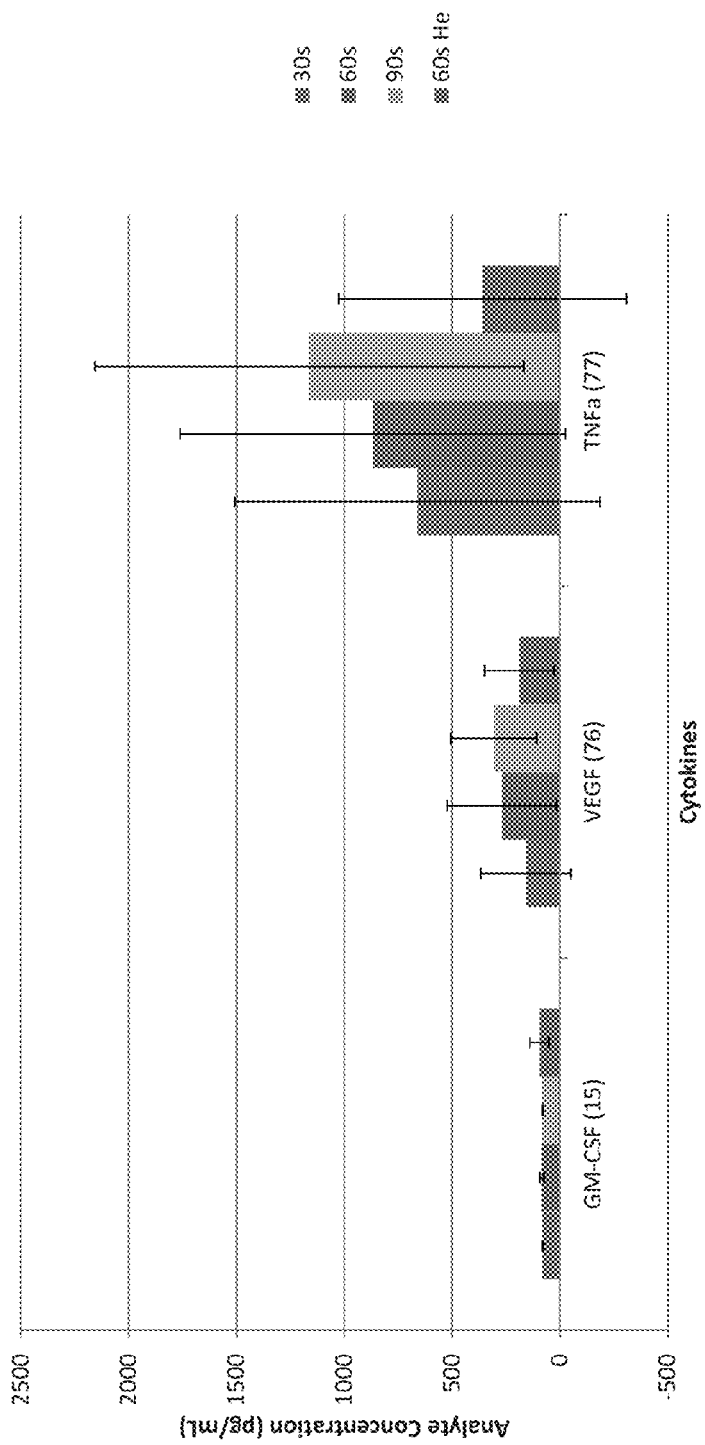

FIG. 2. Cytokines response present in tissue samples at 5 days.

Figure 3:
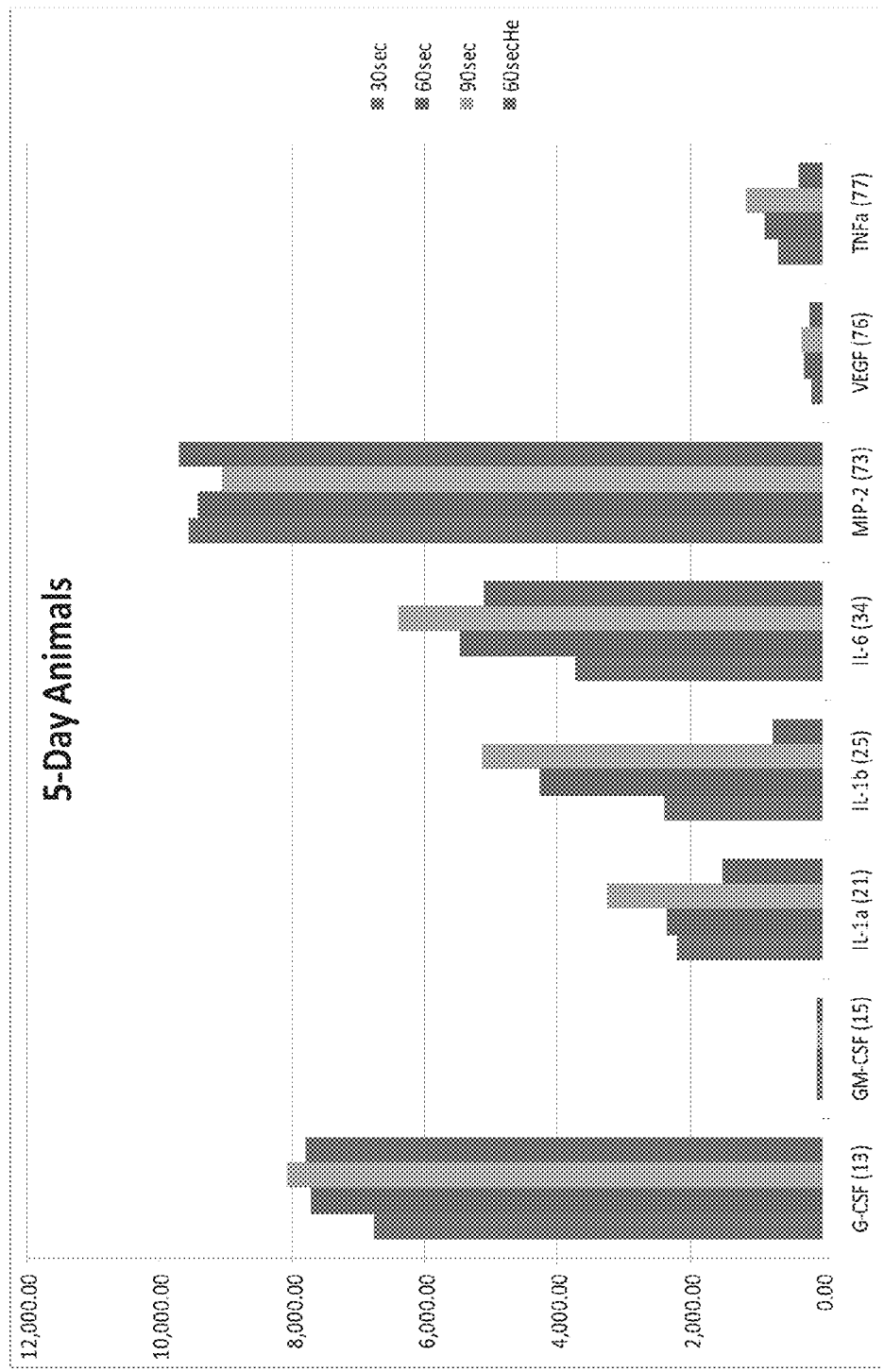

FIG. 3. Cytokines response present in tissue samples at 5 days.

Figure 4:
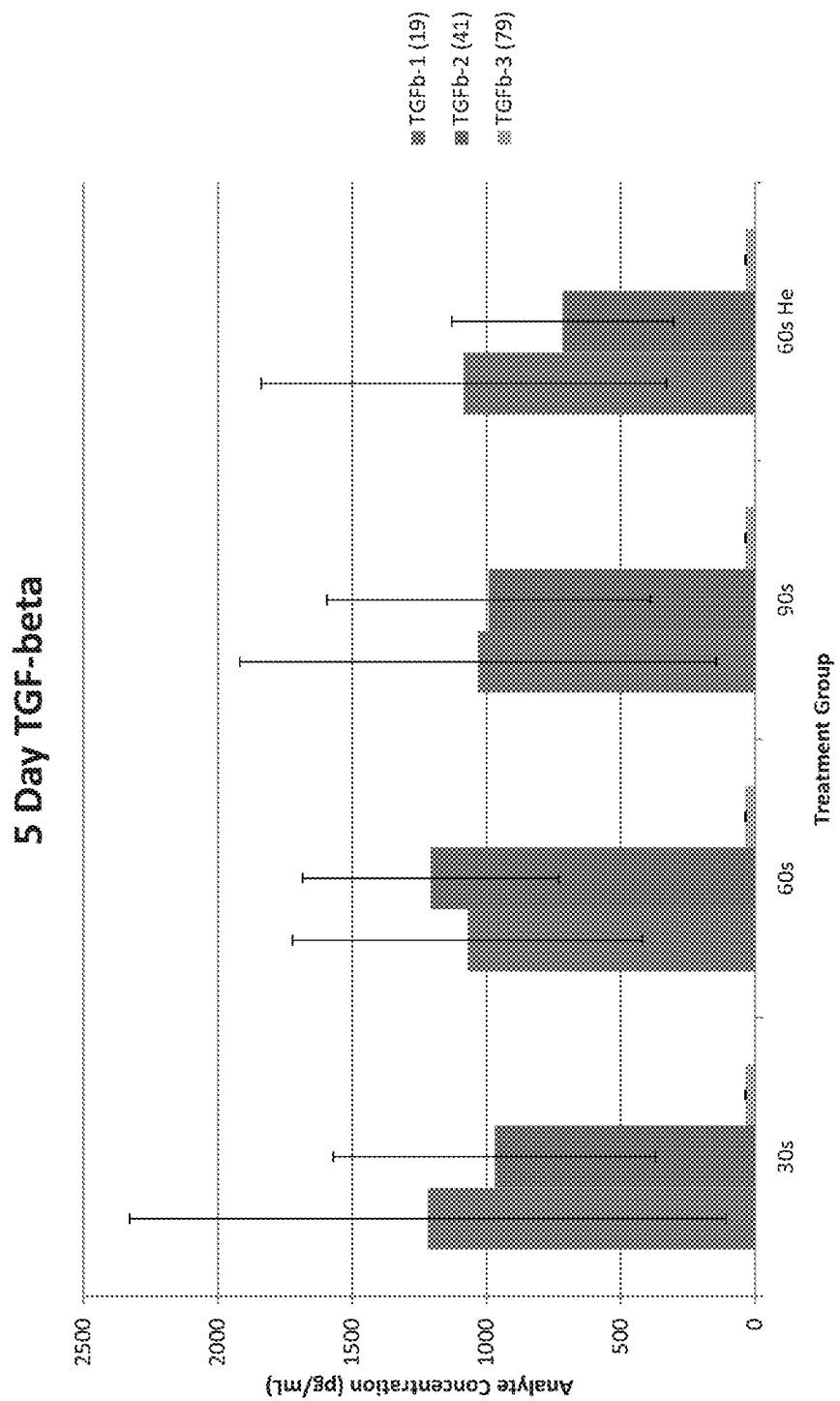

FIG. 4. TGFb response present in tissue samples at 5 days.

Figure 5:
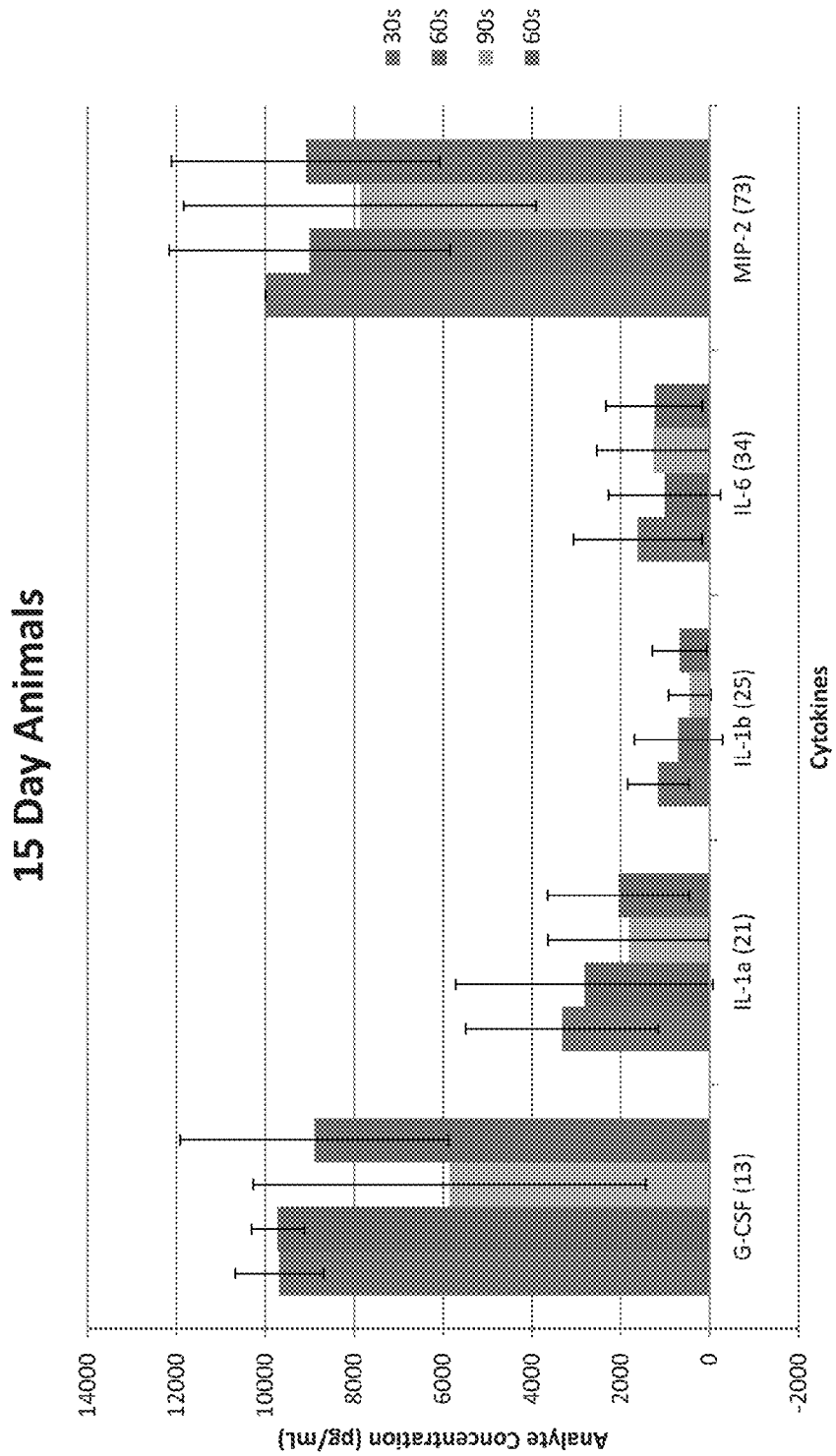

FIG. 5. Cytokine response present in tissue samples at 15 days.

Figure 6:
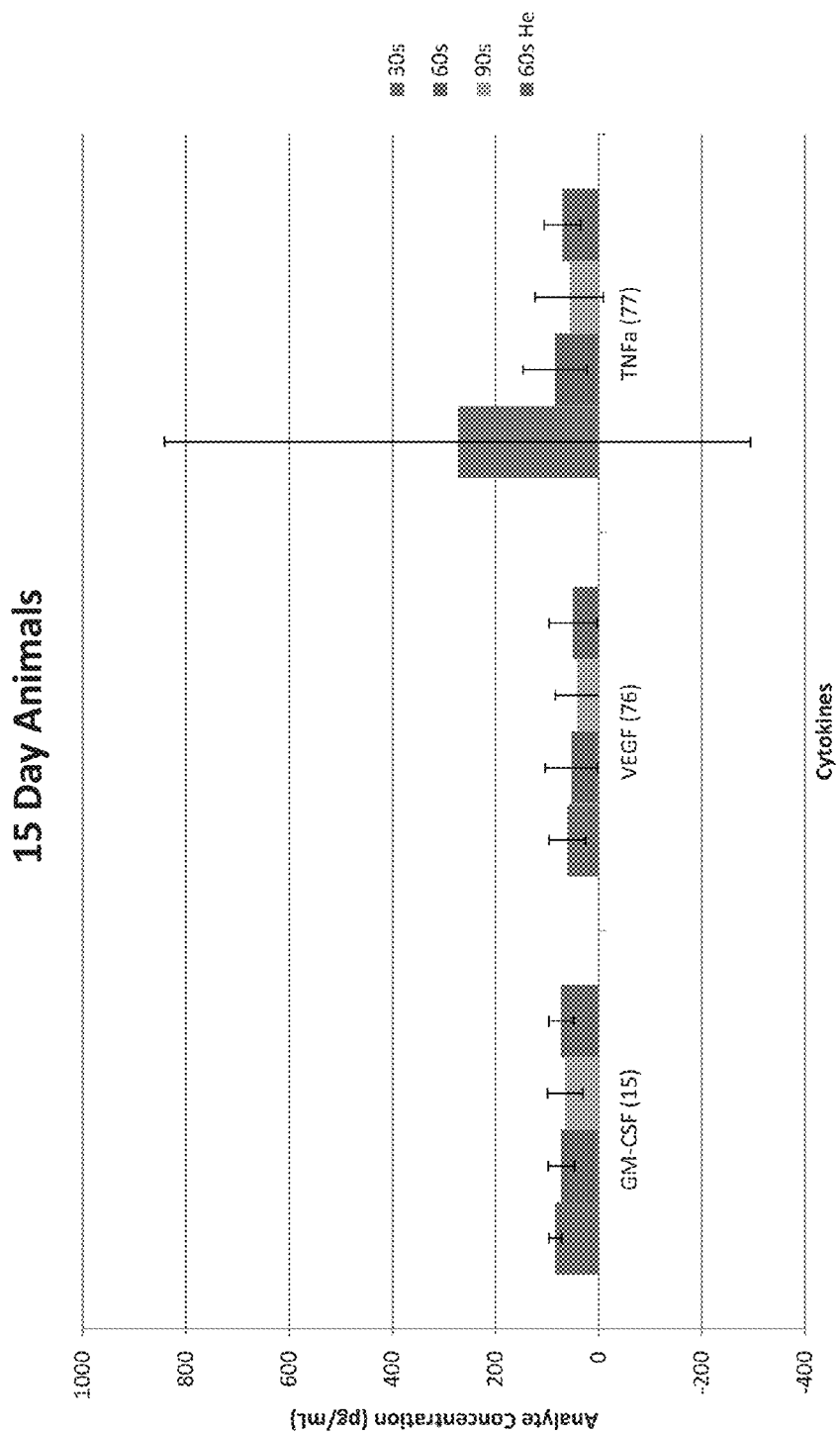

FIG. 6. Cytokine response present in tissue samples at 15 days.

Figure 7:
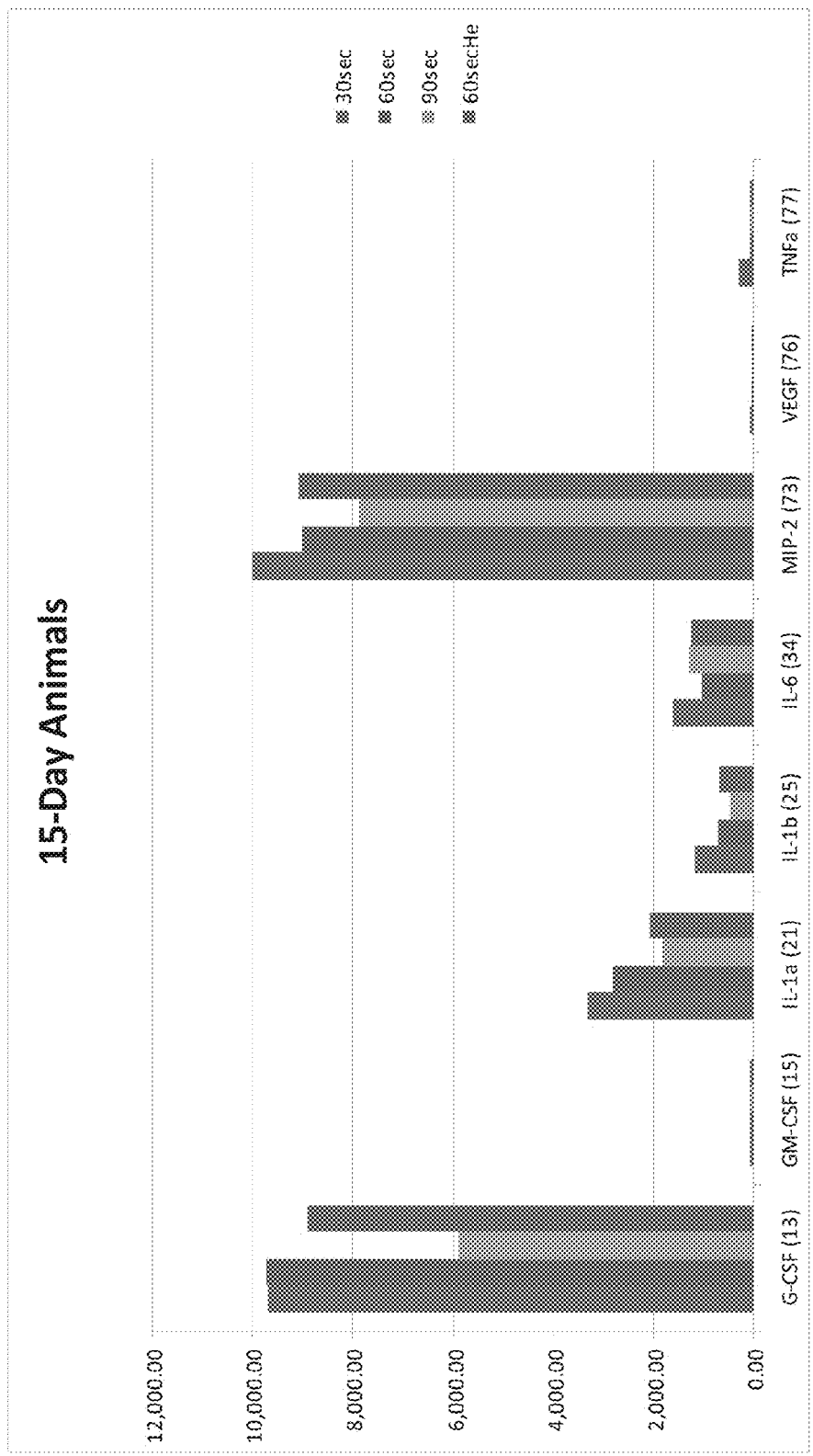

FIG. 7. Cytokine response present in tissue samples at 15 days.

Figure 8:
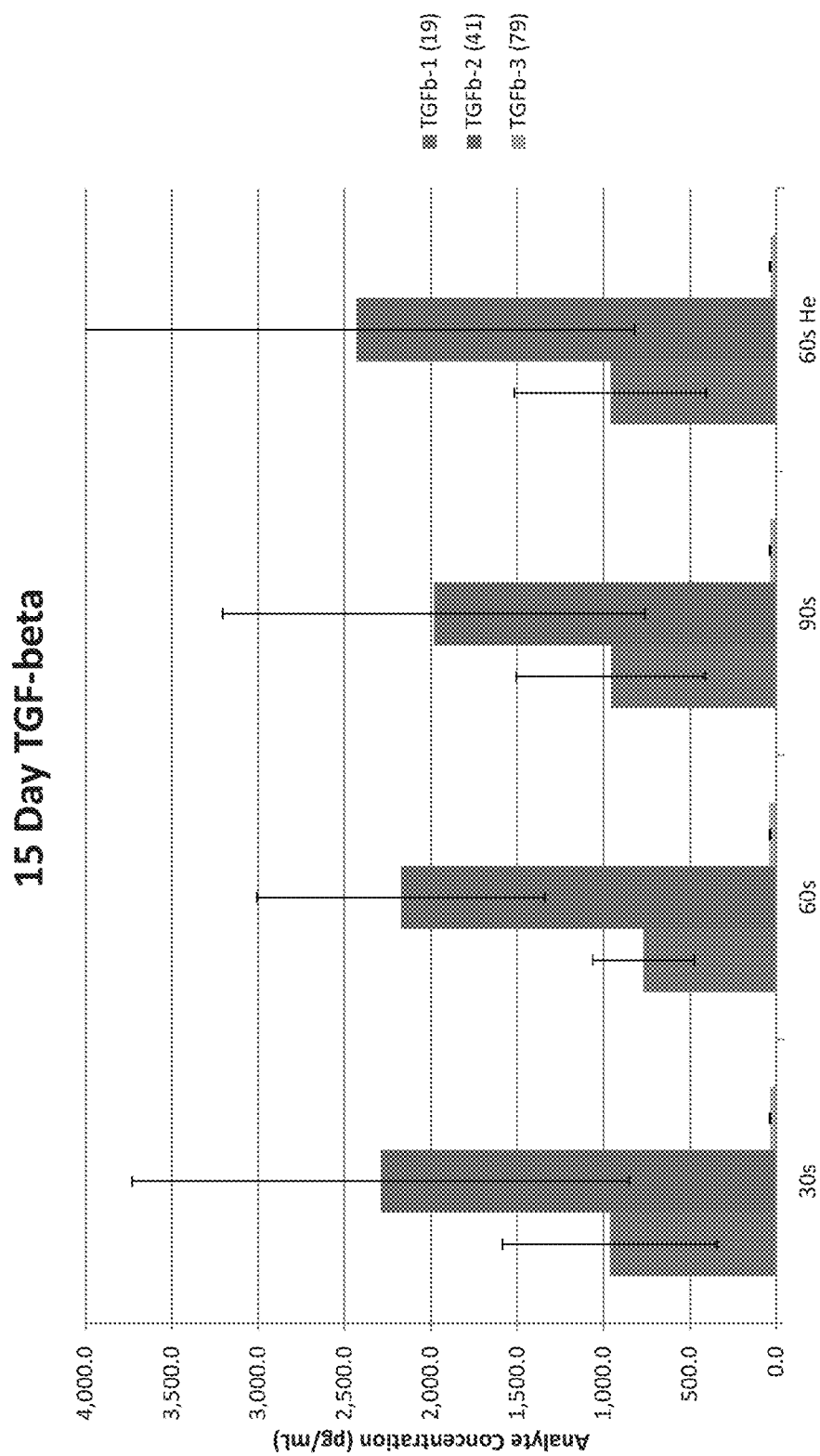

FIG. 8. TGFb response present in tissue samples at 15 days.

DETAILED DESCRIPTION OF THE INVENTION

The present invention relates to methods of treatment comprising administering a therapeutically effective dose of cold plasma. The inventors found that application of cold plasma to a subject resulted in biological effects beyond the suppression of growth of pathological microorganisms at the exposed surfaces. These responses include, for example, but are not limited to, the modulation of inflammatory processes in subcutaneous tissues and the musculoskeletal system.

Inflammation is a natural response to tissue injury. Acute inflammation is a critical step in the successful healing and resolution of an injury. It is when inflammation becomes chronic, either from repetitive injury or dysfunction of the immune system, that inflammation becomes undesirable and problematic. Generally, medications either up-regulate or down-regulate systemic inflammation, but not selectively. Medications that decrease inflammation, such as corticosteroids, can lead to poor healing of injured tissues. Sometimes it is desirable to create an acute injury where a chronic condition exists, to temporarily increase inflammation so the body will initiate healing rather than maintain a high inflammation state without healing. The debridement of a chronic wound and the prolotherapy procedures performed on tendons are examples of this. Without wishing to be bound by any particular theory, harmonic cold plasma can increase the inflammatory response shortly after an acute injury and this up-regulation in, for example IL 1b and TNFa expression, lead to faster healing and lower levels of these same markers of inflammation at day 15. Therefore, without wishing to be bound by any particular theory, treatment of a chronic condition with cold plasma can transition the condition from one of chronic inflammation to acute inflammation, which can then heal through normal course. Similarly, while a short duration cold plasma treatment (e.g., 30 seconds) down-regulates, for example, IL-6 expression and a longer duration treatment (e.g., 90 seconds) increases IL-6 expression 5 days after cold plasma treatment, 15 days after cold plasma treatment IL-6 expression is actually higher in the 30 second group than in the other groups. Without wishing to be bound by any particular theory, the initial up-regulation of inflammatory cytokine cascade by cold plasma treatment leads to faster resolution of inflammation at a later time point. Medically speaking, the ability to modulate inflammation both up and down, and specific inflammatory mediators both up and down is beneficial.

Disclosed herein are methods of treating a skin disease or disorder in a subject in need thereof comprising applying a therapeutically effective dose of cold plasma. In certain embodiments, the skin disease or disorder is associated with an autoimmune or inflammatory disease or disorder. The skin disease or disorder can be associated with, for example, but not limited to, systemic lupus erythematosus, cutaneous lupus erythematosus, scleroderma, psoriasis, dermatomyositis and dermatitis. In one embodiment, the skin disease or disorder is associated with systemic lupus erythematosus. In another embodiment, the skin disease or disorder is associated with cutaneous lupus erythematosus. In specific embodiments, the cutaneous lupus erythematosus is selected from the group consisting of chronic cutaneous lupus erythematosus, subacute cutaneous lupus erythematosus, discoid lupus erythematosus, lupus erythematosus NOS, hypertrophic lupus erythematosus, tumid lupus erythematosus, lupus panniculitis, lupus profundus, cutaneous lupus mucinosis, acute cutaneous lupus erythematosus, chronic cutaneous lupus erythematosus, drug-induced lupus erythematosus, and intermittent cutaneous lupus erythematosus.

In one embodiment, the invention provides a method of treating a mild, moderate, or severe skin disease or disorder associated with lupus erythematosus comprising applying a therapeutically effective dose of cold plasma. A mild skin disease or disorder associated with lupus erythematosus can have a CLASI activity score of between 0 and about 15. A moderate skin disease or disorder associated with lupus erythematosus can have a CLASI activity score of between about 10 and about 25. A severe skin disease or disorder associated with lupus erythematosus can have a CLASI activity score of between about 20 and about 70.

In certain embodiments, a subject treated with cold plasma has a pre-treatment CLASI activity score of between about 1 and about 25. In certain embodiments, a subject treated with cold plasma has a pre-treatment CLASI activity score of less than about 25, about 20 or about 15.

In certain embodiments, a subject treated with cold plasma has a post-treatment CLASI activity score that is lower than the subject's pre-treatment CLASI activity score. The subject can have a post-treatment CLASI activity score of between about 0 and about 10. In certain embodiments, a subject treated with cold plasma has a post-treatment CLASI activity score of less than about 5 or about 10. In specific embodiments, the post-treatment CLASI activity score is detected about 1 day, 2 days or 5 days after cold plasma treatment.

In certain embodiments, a subject treated with cold plasma has a post-treatment CLASI activity score that is reduced by about 10 or about 20 relative to the pre-treatment CLASI activity score. In certain embodiments, a subject treated with cold plasma has a post-treatment CLASI activity score that is reduced by at least about 10 or 20 relative to the pre-treatment CLASI activity score. A skilled artisan understands that 0 is the lowest attainable post-treatment CLASI activity score. In specific embodiments, the reduction in post-treatment CLASI activity score is detected about 1 day, 2 days, 5 days, 15 days, 20 days or 30 days after cold plasma treatment.

In one embodiment, the invention provides a method of reducing flares of a skin disease or disorder comprising applying a therapeutically effective dose of cold plasma. In a specific embodiment, the skin disease or disorder is associated with lupus erythematosus. In some embodiments, flares of a skin disease or disorder associated with lupus erythematosus are associated with an acute increase in CLASI activity score of at least about 3. In specific embodiments, a flare can be associated with an increase in CLASI activity score of at least about 5 or at least about 10.

In certain embodiments, a locally applied therapeutically effective dose of cold plasma has a localized effect of treating the skin disease or disorder at the site the cold plasma is applied. In other embodiments, a locally applied therapeutically effective dose of cold plasma has a systemic effect of treating the skin disease or disorder and thus the application of cold plasma has a therapeutic effect at a site other than or in addition to the site the cold plasma is applied.

In one embodiment, the invention provides a method of treating a skin disease or disorder associated with psoriasis comprising applying a therapeutically effective dose of cold plasma. In specific embodiments, the psoriasis is selected from the group consisting of plaque psoriasis, guttate psoriasis, inverse psoriasis, pustular psoriasis and erythrodermic psoriasis.

In certain embodiments, a subject treated with a course of cold plasma therapy has a post-treatment PASI score that is reduced by about 20% or about 50% relative to the pre treatment PASI score. In certain embodiments, a subject treated with cold plasma has a post-treatment PASI score that is reduced by at least about 20% or about 50% relative to the pre-treatment PASI score.

In another embodiment, the invention provides a method of treating a skin disease or disorder associated with scleroderma comprising applying a therapeutically effective dose of cold plasma. In specific embodiments, the scleroderma is localized scleroderma or systemic scleroderma.

In further embodiments, the invention provides a method of treating a musculoskeletal disease or disorder in a subject in need thereof comprising applying a therapeutically effective dose of cold plasma. The musculoskeletal disease or disorder can be associated with an acute injury or chronic injury. Acute injuries include, but are not limited to, delayed onset muscle soreness (DOMS), muscle strain, torn muscle, tendon strain, torn tendon, ligament sprain, torn ligament, ankle sprain, knee sprain, and finger sprain. Chronic injuries include, but are not limited to, osteoarthritis, tendinitis, tendinopathy and bursitis. In a specific embodiment, the tendinitis is selected from the group consisting of carpal tunnel syndrome, tennis elbow, golfer's elbow, Achilles tendinitis and wrist tendinitis. In another embodiment, the musculoskeletal disease or disorder is chronic joint pain. In a specific embodiment, the bursitis is selected from the group consisting of bursitis under shoulder muscles, at elbows (e.g., epitrochlear bursitis), near the thigh or hip (e.g., trochanteric bursitis), at heel bones (e.g., retrocalcaneal bursitis) or kneecaps (e.g., infrapatellar bursitis). In a further embodiment, the musculoskeletal disease or disorder is associated with an autoimmune or inflammatory disease or disorder. Musculoskeletal autoimmune or inflammatory diseases include but are not limited to rheumatoid arthritis, psoriatic arthritis, and fibromyalgia.

In one embodiment, the administration of a therapeutically effective dose of cold plasma to a subject in need thereof reduces soreness, pain and/or swelling associated with the musculoskeletal disease.

In another embodiment, the administration of a therapeutically effective dose of cold plasma to a subject in need thereof accelerates the recovery from the musculoskeletal disease or disorder. In specific embodiments, the recovery period is at least about one day, two days, three days, four days, five days, six days or seven days shorter following administration of a therapeutic dose of cold plasma.

In one embodiment, the administration of a therapeutically effective dose of cold plasma to a subject in need thereof alleviates the pain and/or swelling associated with osteoarthritis. Osteoarthritic pain can be measured using established clinical protocols, for example, but not limited to, the Visual Analog Scale (VAS), OARSI-OMERACT, Disabilities of the Arm, Shoulder, & Hand Outcome Measure (DASH), Western Ontario and McMaster Universities Arthritis Index (WOMAC), and the Medical Outcomes Study Short-Form (SF-36). In one embodiment, a subject treated with a therapeutically effective dose of cold plasma has a post-treatment VAS score that is about 1 point improved relative to the pre-treatment score. In a further embodiment, a subject treated with a therapeutically effective dose of cold plasma has a post-treatment VAS score that is at least 1 point improved relative to the pre-treatment score. In another embodiment, a subject treated with a therapeutically effective dose of cold plasma has a post-treatment WOMAC score that is about 0.5 to about 1.5 points improved relative to the pre-treatment score. In a further embodiment, a subject treated with a therapeutically effective dose of cold plasma has a post-treatment WOMAC score that is at least about 0.5, or at least about 1, or at least about 1.5 points improved relative to the pre-treatment score.

In additional embodiments, the invention provides a method of treating an autoimmune or inflammatory disease or disorder in a subject in need thereof comprising applying a therapeutically effective dose of cold plasma. In a specific embodiment, the autoimmune or inflammatory disease or disorder is selected from the group consisting of systemic lupus erythematosus, cutaneous lupus erythematosus, rheumatoid arthritis, psoriatic arthritis, systemic sclerosis, scleroderma, psoriasis, polymyositis, dermatomyositis and dermatitis.

In further embodiments, the invention provides a method of suppressing subcutaneous inflammation in a subject in need thereof comprising applying a therapeutically effective dose of cold plasma.

In certain embodiments, the administration of a therapeutically effective dose of cold plasma to a subject in need thereof modulates cytokine expression. The modulation of cytokine expression comprises the down-regulation of pro-inflammatory cytokine expression or the up-regulation of anti-inflammatory cytokines. The down-regulation of pro-inflammatory cytokine expression can be preceded by a temporary increase in their expression. Without being limited to any particular theory, the temporary increase in pro-inflammatory cytokine expression following cold plasma application can indicate the conversion of a chronic inflammation into an acute inflammation which can heal through normal mechanisms. Pro-inflammatory cytokines include, but are not limited to, IL-1-alpha, IL-1-beta, IL-6, IL-11, IL-12, IL-17, IL-18, IL-20, IL-23, IL-33, TNF-alpha, IFN, IFN-gamma, BAFF, LIF, BAFF, CNTF, and GM-CSF. Anti-inflammatory cytokines include, but are not limited to, IL-1ra, IL-4, IL-6, IL-10, IL-11, IL-13, TGF-beta, sTNFRI, sTNFRII, sIL-1RII. See, e.g., Opal et al, *Chest* 117:1162-1172 (2000), Dinarello, *Chest* 118:503-508 (2000). Su et al., *Journal of Biomedicine and Biotechnology* 2012:347141 (2012).

In one embodiment, a method of suppressing subcutaneous inflammation in a subject in need thereof comprises applying a therapeutically effective dose of cold plasma, wherein the post-treatment level of pro-inflammatory cytokine secretion is lower than the pre-treatment level of pro-inflammatory cytokine secretion. In one embodiment, the post-treatment level of pro-inflammatory cytokine secretion is between about 20% and about 90% lower than the pre-treatment level of pro-inflammatory cytokine secretion. In another embodiment, the post-treatment level of pro-inflammatory cytokine secretion is at least about 20% or at least about 50% lower than the pre-treatment level of pro-inflammatory cytokine secretion. In one embodiment, the pro-inflammatory cytokine is selected from the group consisting of IL-1-alpha, IL-1-beta, IL-6, IL-11, IL-12, IL-17, IL-18, IL-20, IL-23, IL-33, TNF-alpha, IFN, IFN-gamma, BAFF, LIF, BAFF, CNTF, and GM-CSF.

In one embodiment, a method of suppressing subcutaneous inflammation in a subject in need thereof comprises applying a therapeutically effective dose of cold plasma, wherein the post-treatment level of anti-inflammatory cytokine secretion is higher than the pre-treatment level of anti-inflammatory cytokine secretion. In one embodiment, the post-treatment level of anti-inflammatory cytokine secretion is between about 20% and 90% higher than the pre-treatment level of anti-inflammatory cytokine secretion. In another embodiment, the post-treatment level of anti-inflammatory cytokine secretion is at least about 50% higher than the pre-treatment level of anti-inflammatory cytokine secretion. In another embodiment, the post-treatment level of anti-inflammatory cytokine secretion is at least about 2 times higher than the pre-treatment level of anti-inflammatory cytokine secretion. In one embodiment, the anti-inflammatory cytokine is selected from the group consisting of IL-1ra, IL-4, IL-6, IL-10, IL-11, IL-13, TGF-beta, sTNFRI, sTNFRII, and sIL-1RII.

In one embodiment, pre-treatment cytokine secretion is determined between about 1 and 30 days before cold plasma treatment. In another embodiment, pre-treatment cytokine secretion level is determined by measuring cytokine levels on more than one occasion before cold plasma treatment. Pre-treatment cytokine secretion level can be determined by combining information from multiple measurements performed before cold plasma treatment, for example, by calculating the average from multiple measurements. Post-treatment cytokine secretion can be determined between about 1 and 30 days after cold plasma therapy. Disease progression can also be monitored using laboratory blood tests, including, but not limited to ANA, ESR and CRP.

In certain embodiments, the administration of a therapeutically effective dose of cold plasma to a subject in need thereof modulates lymphocyte infiltration. The modulation of lymphocyte infiltration comprises the reduction of infiltration by B cells, T cells, T helper cells, Th1 cells or Th17 cells. The modulation of lymphocyte infiltration comprises the increased infiltration of Treg cells.

In one embodiment, a method of suppressing subcutaneous inflammation in a subject in need thereof comprises applying a therapeutically effective dose of cold plasma, wherein lymphocyte infiltration of the subcutaneous tissue after cold plasma treatment is lower than the pre-treatment lymphocyte infiltration. In one embodiment, lymphocyte infiltration is at least about 20% or about 50% lower after cold plasma treatment than before cold plasma treatment. In one embodiment, the lymphocyte is selected from the group consisting of B cells, T cells, T helper cells, Th1 cells and Th17 cells.

In another embodiment, a method of suppressing subcutaneous inflammation in a subject in need thereof comprises applying a therapeutically effective dose of cold plasma, wherein Treg infiltration of the subcutaneous tissue after cold plasma treatment is higher than the pre-treatment Treg infiltration. In one embodiment, Treg infiltration is at least about 20% or about 50% higher after cold plasma treatment than pre-treatment. In another embodiment, Treg infiltration is at least about 3 times or about 5 times higher after cold plasma treatment than pre-treatment.

In one embodiment, the level of cytokine secretion or lymphocyte infiltration is determined in an isolated biological sample. The isolated biological sample can be a skin biopsy, isolated lymph nodes, or isolated lymphatic cells. The pre-treatment sample can be isolated from the subject before administration of cold plasma, from an untreated area of the subject following cold plasma administration or from an untreated control subject. In one embodiment, the effects of cold plasma treatment on cytokine expression or lymphocyte infiltration are manifested about 24 hours or about 36 hours following administration of an effective dose of cold plasma. In another embodiment, the effects of cold plasma treatment on cytokine expression or lymphocyte infiltration are manifested about 2 or about 5 days following administration of an effective dose of cold plasma.

To facilitate an understanding of the present invention, a number of terms and phrases are defined below.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to a dose of cold plasma that is effective to produce a desired effect, which is optionally a therapeutic effect (i.e., by administration of a therapeutically effective amount). For example, a "sufficient amount" or "an amount sufficient to" can be an amount that is effective to reduce swelling of a sprained ankle.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject. In another embodiment, a therapeutically effective amount of cold plasma comprises multiple cold plasma doses delivered hours or days apart. In one embodiment, a therapeutically effective amount of cold plasma dose comprises a series of cold plasma applications delivered seconds or minutes apart. Individual doses can comprise multiple applications of cold plasma delivered seconds or minutes apart.

As used in the present disclosure and claims, the singular forms "a" "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided.

Cold Plasma Processes

Any process known in the art capable of generating cold temperature atmospheric pressure plasma may be used to practice the treatment methods described herein. Atmospheric pressure cold plasma processes typically take as input a source of appropriate gas and a source of high voltage electrical energy, and output a plasma plume. In the case of dielectric barrier discharge (DBD) cold plasmas, the source gas may be the ambient environmental gasses around the electrode and treatment target.

In one embodiment, an atmospheric pressure cold plasma process utilizes positive to negative electrodes in different configurations, which release free electrons into a gas medium. The gas medium can comprise or consist of a noble gas, for example, but not limited to, helium, neon, argon, krypton, xenon or mixtures thereof. In a specific embodiment, the gas medium comprises or consists of helium. The gas medium can further comprise or consist of air, oxygen, nitrogen or mixtures thereof. A skilled artisan understands that when cold plasma processes are performed in ambient air, for example, in a medical office or hospital, the gas medium into which free electrons are released likely comprises some air from the inadvertent mixing of the intended gas medium with ambient air. Alternatively, air can be purposely included in the gas medium into which free electrons are released.

In one embodiment, a method disclosed herein comprises a direct cold plasma treatment. In direct cold plasma treatment, the biological sample treated, for example, but not limited to the subject, organ, tissue or cells treated acts as one of the electrodes of the cold plasma process. In one embodiment, direct cold plasma treatment does not encompass the direct application of voltage by an electrode to the biological sample treated. However, in direct plasma treatment some current can flow through the biological sample treated in the form of, for example, a small conduction current, displacement current or a combination of both. A skilled artisan understands that conduction current should be kept limited to avoid any undesired thermal effect or electrical stimulation of the biological sample.

In one embodiment, atmospheric pressure cold plasma has an average temperature of between about 10° C. and about 50° C., between about 10° C. and about 40° C., between about 15° C. and about 25° C., between about 17° C. and about 22° C., between about 30° C. and about 50° C., between about 35° C. and about 45° C., or between about 35° C. and about 40° C. The cold plasma temperature range acceptable for a particular medical application is determined by the parameters of the application, for example the length of the time period during which plasma is applied to the subject. It is understood that a skilled artisan applying cold plasma therapy is capable of selecting a cold plasma process having an appropriate temperature, voltage, frequency, and duration for the treatment of a particular disease or disorder.

In one embodiment, a method disclosed herein comprises the application of cold plasma generated by a floating electrode dielectric barrier discharge process or by a pin-to-hole spark discharge process. See, e.g., US 2010/0145253 and WO 2010/107744, both of which are incorporated by reference in their entirety.

In one embodiment, a method disclosed herein comprises the application of harmonic cold plasma. Harmonic cold plasma can be generated by discharging cold plasma with simultaneously different rf (radio frequency) wavelengths and their harmonics. Harmonic cold plasma can be generated, for example, by a process described in U.S. Pat. Nos. 7,633,231, 8,005,548, US 2013/0072858, US 2013/0072859, US 2013/0072860, US 2013/0069530, US 2013/0072152, US 2013/0072861, US 2013/0068226, US 2013/0071286, U.S. Appl. No. 61/747,828 and 61/747,428, filed on Dec. 31, 2012, each of which is incorporated by reference for all purposes. In one embodiment, a cold plasma is generated with a repetition frequency in the 1 kHz range. In another embodiment, a cold plasma is generated with a repetition frequency between about 100 Hz and about 10 kHz, between about 100 Hz and about 5 kHz, between about 500 Hz and about 5 kHz, between about 500 Hz and about 2 kHz, or between about 100 Hz and about 2 kHz.

A number of devices capable of generating atmospheric pressure cold plasma are known in the art. In one embodiment, devices described in U.S. Pat. Nos. 7,633,231, 8,005,548, US 2013/0072858, US 2013/0072859, US 2013/0072860, US 2013/0069530, US 2013/0072152, US 2013/0072861, US 2013/0068226. US 2013/0071286, U.S. Appl. No. 61/747,828 and 61/747,428, filed on Dec. 31, 2012 are used to generate atmospheric pressure cold plasma.

Methods of Treatment

The present invention relates to methods of treatment comprising administering a therapeutically effective dose of cold plasma. As noted above, cold plasma can be used to treat skin diseases or disorders associated with an autoimmune or inflammatory disease or disorder, to treat musculoskeletal diseases or disorders or to suppress subcutaneous inflammation in a subject in need thereof comprising applying a therapeutically effective dose of cold plasma. Cold plasma is said to be administered in a "therapeutically effective amount" if the amount administered is physiologically significant. An agent is "physiologically significant" if its presence results in a detectable change in the physiology of a recipient patient. As used herein, the term "subject" is intended to include both human and nonhuman animals. The term "nonhuman animals" of the invention includes all vertebrates, e.g., mammals and non-mammals, such as non-human primates, sheep, dog, cow, etc. In one embodiment, the subject is a human subject.

Lupus erythematosus is an autoimmune disease associated with the presence of autoantibodies directed against components of cell nuclei. Lupus can affect the skin, joints, kidneys, brain, and other organs. Cutaneous lupus erythematosus is categorized into three main entities based on the clinical picture of the disease: chronic cutaneous lupus, subacute cutaneous lupus and acute cutaneous lupus. Patients with chronic cutaneous lupus do not usually develop a systemic form of the disease. Patients with subacute cutaneous lupus can develop additional symptoms, for example, arthritis, while those with acute cutaneous lupus generally have active systemic lupus erythematosus (SLE). The most frequent form of chronic cutaneous lupus is discoid lupus characterized by chronic inflammatory sores on the face, ears, scalp and on other body areas. The lesions can be crusty and scaling and often scar. Lesions and scarring on the scalp can result in permanent hair loss in the affected areas. Subacute cutaneous lupus can present different skin lesions, for example, psoriasis-like lesions with red scaly patches on the arms, shoulders, neck, and trunk and fewer patches on the face, or red ring-shaped lesion with a slight scale on the edges. Lesions associated with acute cutaneous lupus, for example, the "butterfly rash", appear as flattened areas of red skin on the face, reminiscent of a sunburn. These lesions can appear on the arms, legs, and body, and are photosensitive. Though they may discolor the skin, they do not scar. Available treatments include the use of sun protection (SPF+ sunscreen), topical steroids, intralesional steroids, oral steroids, calcineurin inhibitors, pimecrolimus cream or tacrolimus ointment, topical retinoids, antimalarials (e.g., hydroxychloroquine and quinacrine), biologicals (e.g., rituximab, anti-BLys antibody (belimumab)).

Numerous monitoring and scoring scales of skin disorders associated with lupus erythematosus are well known to the skilled clinician, and have been routinely used in the evaluation of lupus erythematosus patients. These include, but are not limited to the CLASI (Cutaneous Lupus Erythematosus [CLE] Disease Area and Severity Index), Skindex and Physician Global Assessment Scale. See, e.g., Klein et al., *Arch Dermatol.* 147(2):203-208 (2011). CLASI provides separate scores for damage and disease activity.

In one embodiment, cutaneous lupus erythematosus can be classified as mild, moderate, and severe based on a CLASI activity score of 0-9, 10-20, and 21-70, respectively.

Psoriasis is a chronic, non-infectious inflammatory skin disease. Psoriasis is characterized by red, scaly patches of skin, which usually have very well defined edges. It is often symmetrical, affecting both sides of the body. The scale is typically silvery white. This typical scale may not be so obvious if the psoriasis affects a body fold such as the armpit or the patient is using emollients regularly. Then it is more likely to be smooth and shiny. There are five types of psoriasis: plaque, guttate, inverse, pustular and erythrodermic. The most common form, plaque psoriasis, is characterized by large flat patches (plaques) covered in scale, most often on elbows, knees and lower back. Psoriasis Area Severity Index (PASI) is a widely used clinical tool for the quantitative assessment of psoriasis symptoms, as well as the effectiveness of psoriasis treatment. PASI is a single score that combines an assessment of the severity of lesions and the extent of affected skin in various body areas. The PASI score ranges from 0 (no disease) to 72 (maximal disease). Available treatments of psoriasis include topical agents (e.g., moisturizers, mineral oils, ointments optionally including an active agent, for example, coal tar, dithranol, corticosteroids, and/or retionoids), phototherapy and systemic agents (methotrexate, cyclosporine, and retinoids).

Scleroderma is an autoimmune disorder affecting the connective tissue that involves changes in the skin, blood vessels, muscles, and internal organs. Localized scleroderma usually affects only the skin on the hands and face. Systemic scleroderma, or sclerosis, may affect large areas of skin and organs such as the heart, lungs, or kidneys. Skin symptoms of scleroderma include Raynaud's phenomenon, hair loss, skin hardness, abnormally light or dark skin, skin thickening, tightness of fingers, hands and forearm, small white lumps beneath the skin, sores on the fingertips and toes, and tight mask-like skin on the face. Available treatments include the use of corticosteroids, immune suppressors (e.g., methotrexate) and NSAIDs.

Dermatitis is an inflammation of the skin, often caused by an allergic reaction. There are different types of dermatitis, including seborrheic dermatitis, atopic dermatitis (eczema) and contact dermatitis. While the symptoms vary with different forms of dermatitis, the symptoms usually include redness of the skin, swelling, itching, skin lesions that sometimes ooze, and scarring. Treatment options include removal of allergen or irritant, topical application of corticosteroids, systemic use of antihistamines to reduce itching.

Delayed onset muscle soreness (DOMS) describes a phenomenon of muscle pain, muscle soreness or muscle stiffness that occurs in the day or two after exercise. This muscle soreness is most frequently felt when after beginning a new exercise program, changing an exercise routine, or dramatically increasing the duration or intensity of the exercise routine. DOMS is generally at its worst within the first 2 days following a new, intense activity and slowly subsides over the next few days. Delayed onset muscle soreness is thought to be a result of microscopic tearing of the muscle fibers. DOMS can be treated by rest, sport massage, gentle stretching, "rest, ice, compression and elevation" (R.I.C.E.), or non-steroidal anti-inflammatory drugs, e.g., ibuprofen, naproxen or aspirin.

Sprain is an injury in a joint, caused by the ligament being stretched beyond its capacity. Commonly injured ligaments are in the ankle, knee, fingers and wrist, e.g., sprained or twisted ankle. This type of injury often occurs in activities such as running, hiking, and basketball. Sprains are associated with swelling, pain and redness in the affected joint. Sprains are commonly graded according to the extent of the injury. A Grade I sprain is a tear of only a few fibers of the ligament. Grade II sprain is one with more than a third of the fibers of a ligament are disrupted without a complete tear in the ligament. Grade III is a complete tear of the ligament. Grade I and II sprains can usually be treated conservatively with treatments such as rest, "rest, ice, compression and elevation" (R.I.C.E.), and non-steroidal anti-inflammatory drugs, e.g., ibuprofen, naproxen or aspirin. Grade III sprains, especially when it affects a weight bearing joint, such as ankle or knee can place individuals at higher risk for permanent instability, and surgical treatment may be necessary.

Strain is an injury to the muscle and/or tendon as a result of strenuous activity. A strain is also referred to as a pull, e.g., muscle pull, tendon pull. Severe strain can result in the tearing of the muscle or tendon with potential damage to small blood vessels causing local bleeding (bruising). Strains may be accompanied by resting pain, weakness of the affected muscle or tendon, swelling, bruising or redness. Strains can be treated by rest, "rest, ice, compression and elevation" (R.I.C.E.), or non-steroidal anti-inflammatory drugs, e.g., ibuprofen, naproxen or aspirin.

Osteoarthritis is a form of arthritis that features the breakdown and eventual loss of the cartilage of one or more joints. Osteoarthritis is generally considered a degenerative disease of aging. The etiology of osteoarthritis is multifactorial involving both mechanical and biochemical factors. Primary osteoarthritis generally refers to osteoarthritis of no known cause. Secondary osteoarthritis generally refers to osteoarthritis associated with an external or internal injury or disease (obesity, repeated trauma or surgery to the joint structures, abnormal joints at birth (congenital abnormalities), gout, diabetes and other hormone disorders). Generalized osteoarthritis affects many joints. Localized osteoarthritis typically affects a single joint, though in some cases, such as with finger arthritis, several joints may be affected. The most common symptom of osteoarthritis is pain in the affected joint(s) after repetitive use. Joint pain of osteoarthritis is usually worse later in the day. There can be swelling, warmth, and creaking of the affected joints. Osteoarthritic pain can be measured using established clinical protocols, for example, but not limited to, the Western Ontario and McMaster Universities Arthritis Index (WOMAC) and the Medical Outcomes Study Short-Form (SF-36). Currently available treatments include the use of pain relievers (e.g., acetaminophen, NSAIDs), corticosteroids, glucosamine and chondroitin sulfate.

Tendinitis is an inflammation, irritation, and swelling of a tendon. It is often associated with acute tendon injuries accompanied by inflammation. Symptoms vary from aches or pains and local stiffness, to a burning that surrounds the whole joint around the inflamed tendon. Swelling may happen along with heat and redness, but not in all cases, there may be visible knots surrounding joint. Available treatments include the use of RICE, NSAIDs, pain medication and steroid injection.

Golfer's elbow, or medial epicondylitis, is an inflammatory condition of the medial epicondyle of the elbow. It is believed to result from repetitive stress to the tendon of the finger flexor muscles in the forearm. Tennis elbow, or lateral epicondylitis, is inflammation, soreness, or pain on the outside (lateral) side of the upper arm near the elbow. It is brought on by occupational activities (e.g., cutting meat, plumbing, and working on cars) and sports (e.g., tennis or other racquet sports) that involve a repetitive wrist motion or a power grip. It is believed that overuse of the extensor carpi radialis brevis (ECRB) causes microtears near its origin at the lateral epicondyle. This leads to the formation of fibrosis and granulation tissue. Available treatments include the common rest, ice, compression and elevation (R.I.C.E.), non-steroidal anti-inflammatory drugs, e.g., ibuprofen, naproxen or aspirin, or steroid injection into the inflamed area in persisting cases. Another treatment option involves injection of a non-pharmacological agent, such as dextrose, into the inflamed tissue (prolotherapy), which creates acute injury to the tendon or ligament. This deliberate acute injury is thought to induce additional acute inflammation that leads to healing of the injury and a subsidence of the chronic inflammatory response underlying the painful condition. These needling procedures can also be conducted "dry," without injecting an irritant, and this acute injury mode has also proved successful in inducing healing and mitigating chronic inflammation. Surgery may also be recommended if the symptoms persist for more than 6-12 months.

Tendinosis or tendinopathy is a degenerative condition of the tendon caused by repetitive microtrauma and inadequate healing response. Tendinosis may result in reduced tensile strength, thus increasing the chance of tendon rupture. Symptoms can vary from an ache or pain and stiffness to the local area of the tendon, or a burning that surrounds the whole joint around the inflamed tendon. Pain frequently worsens during and after activity, and the tendon and joint area can become stiffer the following day as swelling impinges on the movement of the tendon. Therapy generally includes the use of physiotherapy, NSAIDs, local administration of corticosteroids, and prolotherapy.

Bursitis is the inflammation or irritation of a bursa (or protecting sac) that is located in or near the joints. Bursitis is commonly caused by trauma, infection and/or crystal deposits. Bursitis can result from overuse or injury of a joint during work or exercise, incorrect posture at work, or abnormal joint position accompanying, for example, arthritis or bone length differences. Bursitis can also appear in association with other diseases like rheumatoid arthritis, tuberculosis, psoriatic arthritis, gout, or a bacterial infection. The most common locations for bursitis are under shoulder muscles, at elbows (e.g., epitrochlear bursitis), near the thigh or hip (e.g., trochanteric bursitis), at heel bones (e.g., retrocalcaneal bursitis), or kneecaps (e.g., infrapatellar bursitis). Bursitis symptoms vary from local joint pain and stiffness, to stinging pain that surrounds the joint around the inflamed bursa. The pain usually is worse during and after activity. Conventional therapy generally includes resting the affected joint and protecting it from further trauma. Bursae that are not infected were conventionally treated with rest, ice, elevation, physiotherapy, anti-inflammatory drugs and pain medication. Infected bursae can require antibiotic therapy. Surgical therapy may be necessary when conservative treatments fail.

The application of cold plasma according to the present disclosure provides advantages over the conventional treatments for the musculoskeletal diseases and disorders, for example, osteoarthritis, tendinitis, tendinopathy, bursitis, delayed onset muscle soreness (DOMS), muscle strain, torn muscle, tendon strain, torn tendon, ligament sprain, torn ligament, and sprain described above.

Cold plasma can be administered by a variety of methods known in the art. As will be appreciated by the skilled artisan, the dosage, and/or mode of administration will vary depending upon the desired results. Dosage regimens are adjusted to provide the optimum desired response (e.g., a therapeutic response). For example, a single dose can be administered, several shorter doses can be administered over time or the dose can be proportionally reduced or increased as indicated by the exigencies of the therapeutic situation.

A physician or veterinarian having ordinary skill in the art can readily determine and prescribe the effective amount of the cold plasma administration required. For example, the physician or veterinarian could start applying doses of cold plasma at levels lower than that required in order to achieve the desired therapeutic effect and gradually increase the dosage until the desired effect is achieved. In general, a suitable dose, for example, daily dose, of cold plasma will be that amount which is the lowest dose effective to produce a therapeutic effect. Such an effective dose will generally depend upon the factors described above.

In one embodiment, a method described herein comprises the administration of one or more doses of cold plasma. Repeated dose of cold plasma can be administered until a desired response (e.g., a therapeutic response) is achieved. Alternatively, one or more doses of cold plasma can be administered to prevent a relapse or a flare up of a disease or to prevent the recurrence of a symptom or symptoms of a disease.

In one embodiment, a method described herein comprises the administration of at least 1, 3, 5 or 10 doses of cold plasma. In another embodiment, a method described herein comprises the administration of about 1, 3, 5 or 10 or more doses of cold plasma.

Multiple doses of cold plasma can be administered at regular time intervals. In one embodiment, a single dose of cold plasma is administered approximately every four hours, every six hours, or every twelve hours. In another embodiment, a single dose of cold plasma is administered daily or every other day.

A single dose of cold plasma can be characterized by the length of cold plasma application and the distance between an electrode and the surface of the biological sample treated, e.g., the surface of a subject, organ, tissue and cells. In one embodiment, a single dose of cold plasma comprises the application of cold plasma for about 10, for about 20, for about 30, about 90 or about 120 seconds. In another embodiment, a single dose of cold plasma comprises the application of cold plasma for about 1, 2, or 5 minutes. In one embodiment, a single dose of cold plasma comprises the application of cold plasma for at least about 10, at least about 20, at least about 30, at least about 90 or at least about 120 seconds. In another embodiment, a single dose of cold plasma comprises the application of cold plasma for at least about 1, 2, or 5 minutes. In one embodiment, the distance between the applicator tip and the surface of the biological sample treated can be about 2, about 5, about 10, about 20, about 25, about 30 or about 40 mm. In another embodiment, the distance between the applicator tip and the surface of the biological sample treated can be at least about 2, at least about 5, at least about 10, at least about 20, at least about 25, at least about 30 or at least about 40 mm. In one embodiment, the distance between the applicator tip and the surface of the biological sample treated can be less than about 5, less than about 10, less than about 20, less than about 30 or less than about 35 mm. In one embodiment, the distance between the applicator tip and the surface of the biological sample treated can be between about 20 mm and about 30 mm.

If desired, a single effective dose of cold plasma can be administered as two, three, four, live or more sub-doses. Sub-doses can be administered separately at appropriate time intervals to the same area of the biological sample treated, e.g., subject, organ, tissue and cells. In one embodiment, a sub-dose of cold plasma can be administered approximately every 10 minutes, every 30 minutes or every hour. Alternatively, sub-doses of cold plasma can be administered to different areas of the biological sample treated.

In one embodiment, a method of treatment disclosed herein comprises the localized administration, including, for example, topical administration of an effective dose of cold plasma. Localized or topical administration of cold plasma encompasses the application of an effective dose of cold plasma to an affected area of the subject to achieve a desired local therapeutic outcome at the site of cold plasma application. Generally speaking, the cold plasma is emitted in a path to the patient target site. For example, a therapeutically effective dose of cold plasma can be applied to a skin rash of an SLE patient to treat the skin rash, to a painful knee of an osteoarthritic patient to treat the painful knee, or to the elbow of a patient with tennis elbow to treat the elbow. It is understood that the localized or topical administration of cold plasma, for example, to a painful knee of an osteoarthritic patient, or to the elbow of a patient with tennis elbow, treats the internal joint or tendon injury associated with osteoarthritis and tennis elbow, respectively. When used to treat an internal location, such as a joint or tendon injury, the cold plasma is emitted in a path to the skin of the patient in line with the internal location. In certain embodiments, the angle of the energy stream is perpendicular to the internal injury. In certain embodiments, however, the energy stream can be emitted at an oblique angle to the target internal injury.

In one embodiment, the localized or topical administration of a single effective dose of cold plasma comprises the administration of two, three, four, five or more sub-doses to the affected area of the subject. In certain embodiments, localized or topical administration of a therapeutically effective dose of cold plasma has a localized effect of treating a disease or disorder at the site the cold plasma is applied to. In other embodiments, localized or topical administration of a therapeutically effective dose of cold plasma has a systemic effect of treating, for example, a skin disease or disorder and thus the application of cold plasma has a therapeutic effect at a site other than or in addition to the site the cold plasma is applied to. In further embodiments, localized or topical administration of a therapeutically effective dose of cold plasma to an affected tissue, for example, tendon, muscle or bursa has the effect of treating the tissue at a site other than or in addition to the site the cold plasma is applied to.

In another embodiment, a method of treatment disclosed herein comprises the systemic administration of an effective dose of cold plasma. Systemic administration of cold plasma encompasses the application of an effective dose of cold plasma to the subject to achieve a desired systemic therapeutic outcome. Systemically administered cold plasma can be applied to an affected area of the subject or to an unaffected area of a subject. In one embodiment, the systemic administration of a single effective dose of cold plasma comprises the administration of two, three, four, five or more sub-doses to the subject.

In certain embodiments, a method of treatment disclosed herein comprises administering a therapeutically effective dose of cold plasma in combination with the administration of one or more therapeutic modalities, such as, but not limited to, a small molecule agent, hormonal therapy, radiation therapy, biological therapy and/or immune therapy. In one embodiment, the additional therapeutic modality is administered prior to administration of cold plasma. In another embodiment, the additional therapeutic modality is administered after administration of cold plasma. In yet another embodiment, the additional therapeutic modality is administered at the same time as the administration of cold plasma. In certain embodiments, any of the following additional therapeutic modalities can be employed and administered in combination with each other and in combination with cold plasma: systemic corticosteroids, injected corticosteroids, topical corticosteroids, nonsteroidal anti-Inflammatory drugs (e.g., acetylsalicylic acid, ibuprofen, naproxen, indomethacin, nabumetone, tolmetin), antimalarials, immunomodulating agents, immunosuppressive drugs, antibody drugs (e.g., anti-CD20 antibody (e.g., rituximab) and anti-B-lymphocyte stimulator antibody (e.g., belimumomab)), and photo sensitizers such as psoralen, or photodynamics of the porphyrin, chlorophyll, or dye categories.

All of the references cited above, as well as all references cited herein, are incorporated herein by reference in their entireties.

EXAMPLES

Example 1

We utilized a subcutaneous abscess model to determine if the effects of cold plasma treatment are limited to the contact surface or have the potential to affect bacteria, and healing and inflammation of animal tissues through indirect contact.

C57BL/6 mice were injected subcutaneously with 10^7 active cells of *Staphylococcus aureus* bilaterally on their flanks. Animals were prospectively randomized to a treatment and control group, n=14 in each group for a total of 28 animals. Half of the animals received a 30 second cold plasma treatment twice daily while the other half received 30 seconds of helium gas placebo. Cold plasma treatment was administered using a device substantially as described in U.S. Pat. No. 7,633,231. Animals were sacrificed on day 5 (n=7 per group) and day 15 (n=7 per group).

No animals in either group were removed from the study prematurely due to death or severe illness. No rescue actions were required for any mice in either group.

The loss and gain of body weight, as a percentage of initial body weight, is presented below (Table 1). The plasma treated animals lost less weight during the active infection period (Days 5 and 10) and gained more weight following resolution of the infection (Day 15). The weight loss on day 5 is nearly two times greater in the untreated animals and over 5 times greater at day 10. The percent weight gain in the plasma treated group from baseline to day 15 is statistically significant at an alpha level of 0.1 and is not significant in the control group, indicating a strong trend toward improved weight gain in the plasma treated animals. Weight loss/gain is routinely used in animal experiments to indicate failure to thrive, ability to thrive, and general health state.

TABLE 1

Weight Gain/Loss (%) in Abscess Animals

|  | Day 5 | Day 10 | Day 15 |
| --- | --- | --- | --- |
| Control | −0.6 | −2.0 | +1.8 |
| Plasma | −0.3 | −0.4 | +5.0 |
| t-test p value | 0.826 | 0.348 | 0.091 |

The average and standard deviations for abscess size as measured with digital sliding calipers on days 5, 10, and 15 are presented below. Both the right (R) and left (L) abscesses were significantly reduced in size by day 5 when treated with cold plasma ($p<0.05$, $p<0.01$ for L and R respectively), demonstrating a reduction in inflammation. The average treated abscess area was less than one half the size of the average untreated abscess area on the 5th day post injection.

TABLE 2

Abscess Size by Day (mm$^2$)

| | 5 Day Avg | | 5 Day SD | | 10 Day Avg | | 10 Day SD | | 15 Day Avg | | 15 Day SD | |
| --- | --- | --- | --- | --- | --- | --- | --- | --- | --- | --- | --- | --- |
| Group | Left | Right | Left | Right | Left | Right | Left | Right | Left | Right | Left | Right |
| Control | 21.6 | 22.9 | 19.0 | 17.3 | 7.9 | 2.5 | 11.8 | 2.4 | 4.0 | 0.3 | 8.7 | 0.8 |
| Plasma | 10.2 | 8.8 | 5.5 | 5.2 | 2.2 | 1.5 | 3.3 | 1.7 | 1.0 | 0.4 | 1.3 | 1.0 |
| t-test p value | 0.048 | 0.010 | | | 0.263 | 0.405 | | | 0.400 | 0.855 | | |

The number of colony forming units of bacteria that were cultured from the abscess site at the time of sacrifice is presented below. The data demonstrate that active bacteria were present in the abscess tissues 5 days after injection (Table 3). By 15 days, the infection had essentially cleared in both groups. There was a reduction in the average number of CFUs in the plasma treated animals at day 5, but this difference was not statistically significant. Without being limited to any particular theory, the data indicate that reduced abscess size and improved health of cold plasma treated animals does not result from a more efficient elimination of active bacteria from the abscess tissues. Rather, it results from cold plasma mediated reduction of inflammation.

TABLE 16

Subcutaneous Abscess CFUs

| Group | Day 5 Avg | Day 5 SD | Day 15 Avg | Day 15 SD |
|---|---|---|---|---|
| Plasma | 2009 | 2224 | 1.9 | 1.7 |
| Control | 3022 | 3487 | 1.7 | 1.4 |
| t-test p value | 0.529 | | 0.865 | |

Example 2

The effects of cold plasma treatment on a large-scale full-thickness (complete skin removal) wound was examined in C57BL db/db diabetic mice (BKS.Cg-m+/+Leprdb/OlaHsd). Type II diabetes is considered by many experts to be an autoimmune disease that clearly has systemic impact on immune system function. See, e.g., Kohn, et al., *Endocrinology* 146(10): 4189-4191 (2005). A total of 84 mice were included in this study. Mice were divided into 4 treatment groups: (1) untreated controls, helium for 60 seconds twice daily (n=20), (2) cold plasma treatment for 30 seconds twice daily (n=20), (3) cold plasma treatment for 60 seconds twice daily (n=20) and (4) cold plasma treatment for 90 seconds once daily (n=20).

Each mouse received a templated wound measuring 15 mm rostro-caudal by 10 mm medio-lateral under appropriate anesthetic using standard aseptic surgical techniques. All animals were prospectively randomized to their respective treatment groups. All animals were treated with either 30 or 60 seconds of plasma twice daily, or for 90 seconds once daily. The control arm received a "sham" treatment of 60 seconds of unionized helium gas twice daily. The placebo gas treatment was delivered using the same plasma applicator with the power switch in the off position, delivering helium from the same tank as the plasma treated animals. This ensured that the stress level and environmental conditions were comparable between the treatment and placebo groups.

All animals were placed into a custom restrainer during the treatment to minimize movement of the animal and expose the wound for plasma treatment. The plasma applicator was secured in a standard laboratory ring stand with the plasma orifice set 20 mm above the wound surface for all treatment and placebo groups.

Animals were sacrificed at two different time points, day 5 and day 15, to quantify both early and late stage healing process. Death rate, and body weights were measured. Growth factor analysis from wound tissues was performed.

The death rates did not differ between the treatment groups. Body weight was recorded at the time of surgery and again on day 5, day 10, and day 15. Body weight loss is generally used as an indicator of failure to thrive in animal studies. There was no statistical difference in % body weight loss between the treatment groups on days 5 or 10 (Anova p-values of 0.82 and 0.62 respectively). On day 15 there was a trend for reduced weight loss in the 90 second once daily group (Anova p-value 0.078). Post-hoc t-tests confirm that there is a statistically significant difference between both the 90 second-Helium and 90 second-30 second groups.

Growth factor analysis from wound tissues was performed using commercially available assays (e.g., Millipore Mouse Cytokine/Chemokine Assay, Multi-Species TGFb Panel). Tissue from the wound beds of the animals was excised at the time of sacrifice, homogenized in a tissue grinder, and stabilized prior to freezing. Growth factor levels were determined according to the manufacturer's protocols. These panels analyzed specific cytokines responsible for immune cascades, inflammation, and revascularization of tissues. These cytokines were chosen for their ability to explore potential mechanisms of action for the observed changes in wound bed morphology and survival rates throughout this study. FIGS. 1-4 show the cytokine profiles obtained from the early sacrifice (5 day) animals and FIGS. 5-8 show the profiles for the 15 day animals. The data set was manipulated in order to normalize undefined values to a set cutoff reading for analysis purposes (i.e.: >10,000.0 picogram/mL was normalized to 10,000 pg/mL).

Analysis of growth factors from the wound beds of the mice indicated a strong upregulation in proinflammatory and angiogenic cytokines in animals sacrificed at day 5, and a strong reduction in the same cytokines in animals sacrificed on day 15, with respect to control animals. A dose-response effect was clearly evident. Histological analysis of the tissue harvested at 15 days also demonstrated reduced inflammation in the 90 second treatment group when compared to control and other treatment groups. The 90 second treatment group also showed the greatest growth factor increases at day 5 and decreases at day 15. This demonstrates an improved immune response to the acute injury and decrease in chronic inflammation of the injury at day 15.

Type II diabetes is considered by many experts to be an autoimmune disease that clearly has systemic impact on immune system function. See, e.g., Kohn, et al., *Endocrinology* 146(10): 4189-4191 (2005). C57BL db/db diabetic mice develop type II diabetes rapidly along with morbid obesity. The effects of this diabetic gene mutation cause systemic changes to the immune system of the animal. The animals exhibit classic signs of human diabetes such as increased blood glucose levels, difficulty fighting infections, and delayed wound healing. Delayed wound healing observed in diabetic mice correlates with decreased growth factor and cytokine release after tissue injury. Without being limited to any particular theory, the cold plasma treatment induced ramping up of the immune response, as evidenced by increased cytokine and growth factor release immediately after wounding, leading to more rapid acute healing, and a lower likelihood of chronic inflammatory conditions and associated delayed healing.

Chronic musculoskeletal conditions, such as tendonitis, follow a similar principle. To address chronic tendonitis, physicians often perform needling procedures (e.g. prolotherapy) to induce an acute injury to the tendon, which stimulates an injury healing cascade. See, e.g., Nair, *Translational Research* 158(3): 129-131 (2011). This cascade, including a rapid growth factor release, converts the chronic inflammation to acute healing. Without being limited to any particular theory, because cold plasma treatment induces a similar increase in growth factor production in animals suffering from a chronic inflammation condition, the same effects can be achieved with plasma therapy.

Example 3

This example describes the use of cold plasma to treat tendinitis in a human patient. Achilles tendonitis is a condition of irritation and inflammation of the large tendon in the back of the ankle. Achilles tendonitis is a common injury that tends to occur in recreational athletes. The main complaint associated with Achilles tendonitis is pain behind the heel. The pain is often most prominent in an area about 2-4 centimeters above where the tendon attaches to the heel. Patients with Achilles tendonitis usually experience the most significant pain after periods of inactivity.

Patients with Achilles tendonitis are treated with cold plasma generated as described herein. Patients are treated with cold plasma once a day until the symptoms of Achilles tendonitis disappear, or in certain cases once a day until 3-5 days after the symptoms of Achilles tendonitis disappear. Each treatment comprises the application of cold plasma for between about 30 second and about 3 minutes to the skin overlying the affected tendon. The cold plasma can be administered prior to, concurrently with, or after standard therapy regimens, such as immobilization, ice application and anti-inflammatory medication. Patients are monitored to determine whether cold plasma treatment has resulted in a positive response, for example, reduction in the time required for recovery from the tendonitis, reduction in the intensity of symptoms, e.g., pain, or reduction in the use of anti-inflammatory medication.

Example 4

This example describes the use of cold plasma to treat ankle sprain in a human patient. An ankle sprain is an injury to the ligament in the ankle. Common symptoms associated with an ankle sprain are pain with swelling and bruising.

Patients with ankle sprain are treated with cold plasma generated as described herein. Patients are treated with cold plasma once a day until the symptoms of ankle sprain disappear. In specific embodiments, patients are treated until the swelling or joint pain disappears. In further specific embodiments, patients are treated until the complete rehabilitation of the damaged ankle. The daily treatment comprises the application of cold plasma for between about 30 second and about 3 minutes to the affected ankle. The cold plasma can be administered prior to, concurrently with, or after standard therapy regimens, such as immobilization, ice application and anti-inflammatory medication. Cold plasma can also be administered prior to, concurrently with, or after standard rehabilitation therapy, such as range of motion exercises. Patients are monitored to determine whether cold plasma treatment has resulted in a positive response, for example, reduction in the time required for recovery, reduction in the intensity of symptoms, e.g., swelling or pain, or reduction in the use of anti-inflammatory medication.

Example 5

This example describes the use of cold plasma to treat psoriasis in a human patient. Psoriasis is a chronic, non-infectious inflammatory skin disease. Psoriasis is characterized by red, scaly patches of skin, which usually have very well defined edges. It is often symmetrical, affecting both sides of the body. The scale is typically silvery white.

Patients with psoriasis are treated with cold plasma generated as described herein. Patients with active psoriasis are treated with cold plasma once a day, once every other day, twice weekly or once a week until the symptoms of psoriasis improve. Psoriasis symptoms are monitored using the Psoriasis Area Severity Index (PASI). In one embodiment, a clinically relevant improvement in psoriasis symptoms is a 50% or 75% reduction in PASI score. During remission, patients with psoriasis can be treated with cold plasma once a week, once every other week or once a month. A single treatment comprises the application of cold plasma for between about 30 second and about 3 minutes to the affected skin area. The cold plasma can be administered prior to, concurrently with, or after standard therapy regimens, including topical agents (e.g., moisturizers, mineral oils, ointments optionally including an active agent, for example, coal tar, dithranol, corticosteroids, and/or retionoids), phototherapy and systemic agents (methotrexate, cyclosporine, and retinoids).

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method of suppressing subcutaneous inflammation in a subject in need thereof comprising applying to said subject a therapeutically effective dose of cold plasma, wherein the cold plasma is an harmonic cold plasma generated by discharging cold plasma with simultaneously different RF (radio frequency) wavelengths and their harmonics.

2. The method of claim 1, wherein the subcutaneous inflammation is associated with a subcutaneous infection.

3. The method of claim 2, wherein the subcutaneous infection is an abscess.

4. The method of claim 3, wherein the applying the therapeutically effective dose of cold plasma reduces a size of the abscess.

5. The method of claim 1, wherein the applying the therapeutically effective dose of cold plasma includes applying the therapeutically effective dose of cold plasma locally to an affected area of a body of the subject.

6. The method of claim 5, wherein the applying the therapeutically effective dose of cold plasma locally alleviates at least one symptom of the subcutaneous inflammation at a site of the cold plasma application.

7. The method of claim 6, wherein the applying the therapeutically effective dose of cold plasma locally alleviates swelling at the site of the cold plasma application.

8. The method of claim 1, wherein the applying the therapeutically effecive dose of cold plasma includes applying the therapeutically effective dose of cold plasma systemically to a body of the subject.

9. The method of claim 1, wherein the cold plasma is formed using ambient air.

10. The method of claim 1, wherein the cold plasma is formed using a noble gas.

11. The method of claim 10, wherein the noble gas is selected from a group consisting of helium, neon, argon, krypton, xenon and mixtures thereof.

12. The method of claim 10, wherein the harmonic cold plasma is produced by a process comprising injecting the noble gas onto an electrode comprising a plurality of electrode plates positioned in substantially parallel, spaced-apart fashion, a surface area of an upstream electrode plate greater than a surface area of a downstream electrode plate, the plurality of electrode plates supported by a support rod, the support rod extending through each of the plurality of electrode plates and supporting a distance therebetween;

supplying radio-frequency energy to the support rod to thereby energize the noble gas via the plurality of electrodes; channeling the energized noble gas through an orifice of a first toroidal magnet having a first alignment; channeling the energized noble gas emerging from the orifice of the first toroidal magnet onto an induction grid in frequency harmony with the plurality of electrodes, the induction grid comprising: a central capacitance element; and a plurality of metal rods, each having an outer capacitance element affixed at opposed ends, the plurality of metal rods approximately symmetrically arrayed about the central capacitance element at increasing radial distances from an innermost rod to an outermost rod; supplying power to the central capacitance element and to the outermost rod to further energize the noble gas; and channeling the cold plasma through an orifice of a second toroidal magnet having a second alignment opposite the first alignment and thereby output the harmonic cold plasma.

* * * * *